United States Patent
Svetliza

[19]

[11] Patent Number: 6,086,205
[45] Date of Patent: Jul. 11, 2000

[54] APPARATUS AND METHOD FOR SIMULTANEOUS BILATERAL RETINAL DIGITAL ANGIOGRAPHY

[75] Inventor: Eduardo Svetliza, Raanana, Israel

[73] Assignee: Medibell Medical Vision Technologies Ltd., Haifa, Israel

[21] Appl. No.: 09/175,571

[22] Filed: Oct. 20, 1998

[30] Foreign Application Priority Data

Oct. 21, 1997 [IL] Israel ......................................... 122114

[51] Int. Cl.$^7$ ....................................................... A61B 3/10
[52] U.S. Cl. .............................................................. 351/221
[58] Field of Search ..................................... 351/205, 206, 351/211, 221; 600/431; 356/51

[56] References Cited

U.S. PATENT DOCUMENTS

| | | | |
|---|---|---|---|
| 3,893,447 | 7/1975 | Hochheimer et al. .................. | 351/206 |
| 5,543,866 | 8/1996 | Van De Velde .......................... | 351/221 |

*Primary Examiner*—George Manuel
*Attorney, Agent, or Firm*—Edward Langer

[57] ABSTRACT

A novel apparatus and method for simultaneous bilateral retinal digital angiography. The apparatus is provided as an optical system containing two optical modules which act as retinal ophthalmoscopes with image capture capacity in real time. Each optical module is positioned in front of one eye, allowing simultaneous imaging of both retinas on a screen placed in a position convenient for the operator, allowing the operator to visualize both images simultaneously. The invention provides for the use of agents of contrast for angiographical study. In a preferred embodiment, the operator aligns and focuses the apparatus manually with the aid of a joystick. A trigger located on or near the joystick allows image capturing. In another preferred embodiment, the apparatus is controlled by a semi-automated mode of operation, in which the optical modules are aligned manually while fine alignment for pupil centralization is done by a motorized system. In yet another preferred embodiment, a fully automated apparatus is provided in which a plurality of infrared detectors are used to align the apparatus and at least one infrared beam is used for focusing. The illumination system may be provided as a viewing light source and strobe lamp with fiber optic guides or as a scanning laser beam.

20 Claims, 11 Drawing Sheets

APPARATUS AND METHOD FOR SIMULTANEOUS BILATERAL RETINAL DIGITAL ANGIOGRAPHY

FIELD OF THE INVENTION

The present invention relates to medical equipment for opthalmological uses, and, in particular to retinal imaging.

BACKGROUND OF THE INVENTION

The process of angiography involves the visualization of the circulation system through injection of dyes. Angiography can be done on various parts of the body and can be especially important in diagnosing circulation problems in the eye, such as occlusion of the central artery. Diabetics especially suffer from vascular problems in the eye, including those with juvenile diabetes, where the disease may become aggressive, causing impaired vision. In situations involving occlusion of blood vessels in the eye, rapid diagnosis can be essential for saving the sight of the patient. Continuous oxygenated blood flow to the area is necessary to maintain physiological function of the different structures of the eye. When the blood supply is interrupted the retina is affected and sight begins to deteriorate. In many situations the lapse of time between the moment a person senses impaired sight and the moment of treatment is crucial to restore the lost vision to the previous state. Unless the occlusion is extreme, routine fundoscopy of the eye will not reveal the disease. In less severe cases the examination may show an apparently clear fundus. Angiography is necessary to assure the pathological findings of the disease in extreme cases and to ascertain the presence of disease in less severe cases.

Current equipment makes it difficult for the ophthalmologist to confirm a diagnosis of artery occlusion through imaging techniques. This is especially so in cases where the arterial circulation is only partially occluded. In cases of partial occlusion the ophthalmologist should see a delay in the infusion of the agent of contrast into the eye because of the slow passage through the narrowed or occluded blood vessel. However, current technology does not enable the ophthalmologist to simultaneously angiographically compare the problematic retina with the other healthy retina as a point of reference. The time difference necessary in examining each retina separately makes a comparison of this type impossible. In an examination of a diabetic where the disease may be affecting the eyes, information from an angiography study is already available within twenty seconds post-injection. In this early phase the agent of contrast reaches the peak degree of fluorescence due to its high concentration.

The most popular equipment in use currently is the fundus camera (such as the CF-60UVi available from Canon Inc., Lake Success, N.Y. 11042). Using the current conventional method of attempting to measure in both eyes, the procedure consists on "jumping" the camera from eye to eye while the agent of contrast circulates it is not possible to study both eyes within a twenty second period. Understandably, much vital information is lost to the ophthalmologist in the time it takes to move the camera from eye to eye and readjust it.

The procedure of retinal angiography is very dynamic and the uncaptured images are very important to the analysis of the results of the examination. Therefore, the patient is required to return for a second analysis during which the procedure is repeated. This second analysis cannot be done for at least 48 hours, until the agent of contrast has dissipated. This need for a second procedure, including a second injection, causes undue discomfort and inconvenience to the patient, while incurring a loss of a minimum of 48 hours in diagnosis time, time which may be crucial to perform the therapy which would restore the sight of the patient.

In the case of a patient suffering from Aging Macular Degeneration (AMD), this time delay causes a serious problem affecting the ability of the ophthalmologist to attempt to treat the disease. AMD is a disease which affects the macula, the part of the retina responsible for acute sight, by effecting changes in and destroying the different layers of the retina, including the photoreceptors. A certain percentage of the patients reveal a pathological growth of new vessels emerging from the choroidal vascular network. When this phenomenon occurs, a rapid decision of laser therapy intervention is required to destroy the membrane, thereby preserving the macula. Laser therapy must be performed within 72 hours of visualization of the pathological growth by retinal angiogram, so as to ensure that the disease has not progressed. Because of the inherent delay in current technology it is not possible to help a patient where the disease has attacked both eyes.

Attempts have been made using current technology to construct an apparatus capable of doing simultaneous bilateral retinal angiography, however there is as of yet no apparatus which is sufficiently simple and convenient to use so as to allow a technician to operate it. Several problems of operation are difficult to overcome with the existing technology. A simplistic approach would be to combine two standard single retinal cameras, placing one in front of each eye. The paper by De Kerk, et al. (Journal of Ophthalmology, December 1979) discloses an apparatus composed of two cameras for simultaneous bilateral angiography, requiring an operator for each of the two cameras. This is clearly a research tool and not an apparatus to be used in a doctor's office or hospital setting. First, the pupil distance does not allow the proper alignment of two single retinal cameras due to the bulk of the devices. Second, the handling by two operators causes unnecessary discomfort for the patient as both are independently attempting to align the patient's eye with the camera that they are operating. Third, the effectiveness of the procedure is low because of the complicated management necessary. Each operator uses his own judgment as to when to capture the image which may not necessarily compare with the other operator's image. Clearly the cost of two complete retinal camera systems makes analysis of this type very expensive. In addition, the De Kerk apparatus uses still camera film technology, which does not supply the necessary information on dye movement dynamics for diagnosis.

Scanning laser beam technology is the new trend in ophthalmic equipment. Use of scanning laser beam technology as disclosed in U.S. Pat. No. 4,213,678 to Pomerantzeff, U.S. Pat. No. 4,579,430 to Bille, U.S. Pat. No. 4,968,130 to Hideshima et al., and U.S. Pat. No. 5,066,116 to Sekine allows examination of the findus at a smaller pupil size and with a much lower intensity of light. However, these have only been used to observe one eye at a time.

In addition, conventional fundus cameras provide viewers through which the operator observes the eye. From this perspective it would not be possible for the operator to focus on two eyes simultaneously.

Therefore, it would be desirable to provide an apparatus for retinal imaging which would be capable of performing retinal angiography on both eyes simultaneously in an easy to operate fashion, providing significantly more accurate results of the examination without the need for a second examination, saving time and causing less discomfort to the patient, while providing a cost-effective apparatus for healthcare facilities with restricted budgets. Such an apparatus would allow acquisition of new information and thereby improve eye care.

SUMMARY OF THE INVENTION

Accordingly, it is the object of the present invention to overcome the problems associated with the prior art and provide an apparatus for simultaneous bilateral retinal digital angiography.

In accordance with a preferred embodiment of the present invention, there is provided an apparatus for diagnosis of retinal disorders comprising:

a pair of means for optically forming independent retinal images, each forming means being separately adjustable for observation of an eye, each of said forming means comprising;

means for alignment of said forming means in front of the eye;

means for illumination of the interior of the eye; and means for focusing said retinal image, and at least one display means for displaying each of said pair of retinal images enabling simultaneous bilateral retinal digital angiography for diagnostic analysis.

In a preferred embodiment, the apparatus is provided as an optical system containing two optical modules which act as retinal ophthalmoscopes with image capture capacity in real time. Each optical module is positioned in front of one eye, allowing imaging of the retina, the posterior segment of the eye. In one preferred embodiment of the invention, each optical module is attached to a separate movable base, with each optical module being independently controlled. By way of example, a joystick is controlled by the operator, moving each optical module in any of three planes of movement (X,Y,Z), so as to align the apparatus in front of the eye while imaging the retina through the pupil. In this embodiment, all the commands for alignment and fine adjustment are done manually by way of a mechanical gear system. Focusing is accomplished through camera positioning and not through movement of the camera lens. Triggers are located on or near the joysticks and are depressed to initiate the simultaneous acquisition of image. Depression of either trigger will capture images from both optical modules, as the wiring of both triggers is connected. This enables the operator to use either hand to capture the image, at his convenience.

In another preferred embodiment, the apparatus is controlled by a semi-automated mode of operation. This mode aligns the optical modules manually while the fine alignment for pupil centralization is done by a motorized system. The manual and motorized systems work independently of each other. The commands for the motorized alignment are located near the joystick allowing the operator free displacement of the modules corresponding to the optical axis of each eye. The focus of the images is achieved manually by two knobs located beside each module.

In yet another preferred embodiment, a fully automated apparatus is provided in which a plurality of infrared detectors are used to align the apparatus and at least one infrared beam is used for focusing. The detectors are distributed in approximately four cardinal points around the front panel of each module so as to detect the edge of a dilated pupil. The optical modules are centralized with the optical axis of the eye. In this embodiment, the image is constantly focused due to an infrared beam which passes through the optical module and is projected onto the retina through the pupil. The beam continuously measures the distance between the retina and the focal plane determining focusing parameters. A small motor is provided for forward and backward motion of the optical elements of the module allowing free focusing of the optical image in response to the focusing parameters. This design maintains a constant auto-focused image.

Other features and advantages of the invention will become apparent from the following drawings and description:

BRIEF DESCRIPTION OF THE DRAWINGS

For a better understanding of the invention with regard to the embodiments thereof, reference is made to the accompanying drawings, in which like numerals designate corresponding elements or sections throughout and in which.

DETAILED DESCRIPTION OF A PREFERRED EMBODIMENT

Figure 1:
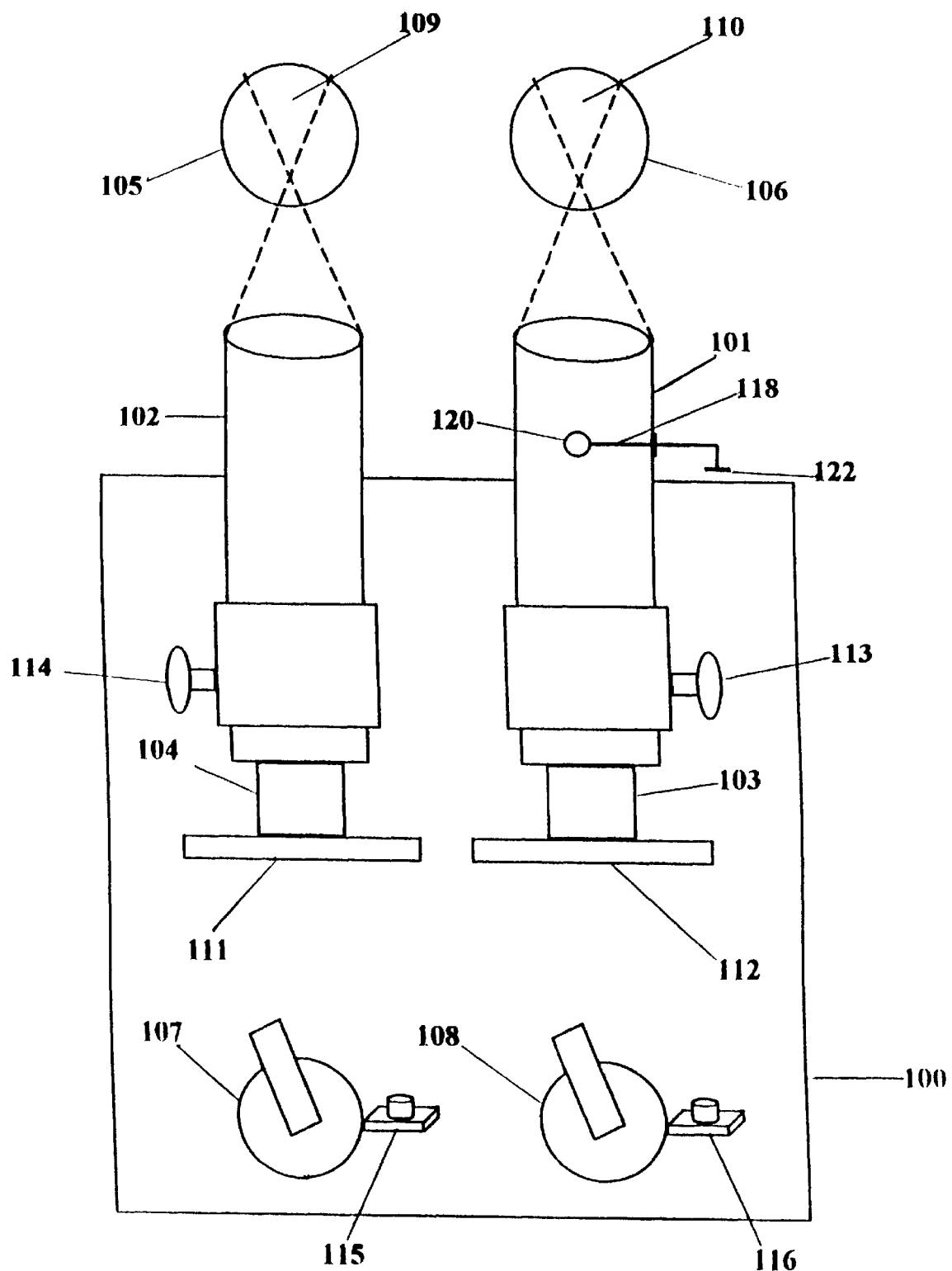
FIG. 1 is an overhead view of the apparatus of the present invention constructed and operated in accordance with the principles of the invention.

Referring now to FIG. 1, there is shown an overhead view of the apparatus of the present invention constructed and operated in accordance with the principles of the invention. Optical modules 101, 102 image the fundus of the eye, working independently of one another. Modules 101,102 are of similar optical qualities such as resolution, working distance and chromatic aberrations. This similarity is necessary to acquire realistic images for comparison, although by nature there exist nonsymmetrical physiological characteristics, such as eye size, eye height, shape of the eyeball, difference in refractive power. Modules 101,102 are adapted to overcome these physiological differences in the condition of the respective eye by way of joysticks 108, 107, respectively. Joysticks 107 and 108 provide movement on three planes (X,Y,Z) so as to align the apparatus in front of the eye while imaging the retina through the pupil. This can be accomplished by means of widely used technology, such as a slit lamp 900 developed by Haag-Streit AG, Koniz, Switzerland. Joystick 107 is controlled by the left hand of the operator, aligning module 102. Joystick 108 is controlled by the right hand of the operator, aligning module 101.

Module 101 obtains an image from right eye 105 via field of view 109. Module 102 obtains an image from left eye 106 via field of view 110. In the rear of modules 101, 102 are coupled electronic video cameras 103, 104 respectively. Cameras 103, 104 allow simultaneous images from eyes 105, 106 to be displayed on monitors 111,112, respectively. Knobs 114, 113 focus the images acquired from cameras 104,103, respectively. Triggers 115, 116 located on or near the joystick freeze the images obtained from cameras 104, 103 and capture the simultaneous images.

Although conventional retinal cameras use viewers for looking at images, in the case of simultaneous bilateral retinal imaging, it is necessary to use a monitor to permit the operator to be distanced from the viewing surface. It is only at a certain distance from a single monitor that the operator can absorb two separate images simultaneously.

Fixation of eye movement to allow positioning of the retina in the required field may be accomplished by placing of mechanical needle 118 in the optical path, such that needle head 120 creates a dark spot seen in the light beam emerging from the apparatus. The operator may move needle 120 by means of handle 122 so as to cause the patient to realign the eye. The apparatus rests on table 100.

Figure 2:
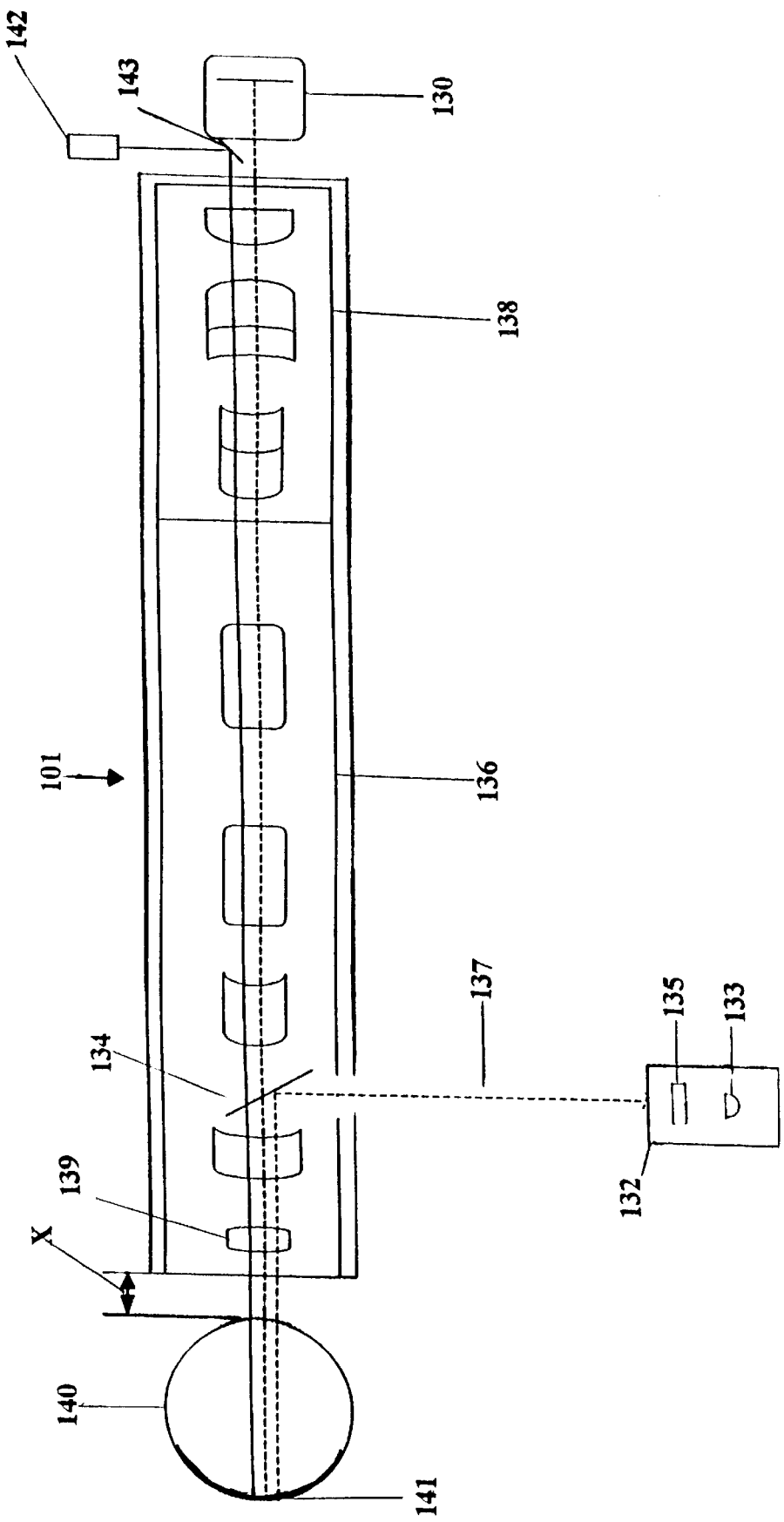
FIG. 2 is a schematic drawing of the optical pathway.

FIG. 2 shows a schematic diagram of the optical light path of a single optical module. By way of example, the light path emerging from optical module 101 is captured by image capturing element 130, such as charge coupled device (CCD) which may include means for image analysis and data storage, such as optical, magnetic or magneto-optic storage media, a cathode ray tube (CRT), a printer and the like.

Optical module 101 is brought to a distance of approximately 20–40 mm from eye 140 to be examined as shown by arrow X. Illumination light 132 is provided separately from the optical modules. In one embodiment, the projected light is incorporated into the optical pathway through beam splitter 134. Beam splitter 134 causes rays of light from illumination element 132 to fall on the retina. Illumination element 132 is composed of halogen lamp 133 and strobe lamp 135. Illumination element 132 is connected to two illuminating fiber optic bundles 137 each of which are connected to one of the optical modules. Fiber optic bundles 137 bring the light to beam splitter 134. The use of flexible fiber optics allows the use of only one illumination element for both optical modules, an economical aspect. In addition, by using the flexible fiber optics, the illumination element can be placed at a point separate from the optical modules so that alignment and focusing of the optical modules will not require moving the illumination element. The fiber optic bundles will follow the movements of the optical modules, due to their flexibility. The reflected light passes through the optical element via the beam splitter to image capturing element 130. Filters are properly positioned in the light pathway for excitation and absorption of dye wavelengths.

Focusing may be accomplished by means of an infrared beam emanating from infrared source 142 which is deflected by small mirror 143 into the optical pathway of the apparatus. Infrared source 142 continuously measures the distance to retina 141. The value acquired from this measurement is calculated to the value the camera needs to be moved forward or backward by a motor so as to maintain a constant focused image. This technique is widely used in still digital and film cameras as well as in video cameras for home use.

When the apparatus is equipped with an image scanning laser which both illuminates and scans simultaneously, detection is enabled at a small pupil diameter so that there is no need for dilation, saving the patient time and discomfort. (According to the method of Webb, R. H. et al., Flying Spot TV Ophthalmoscope, in Applied Optics, Sep. 1, 1980) In addition, only one percent of the illumination is necessary as compared with common ophthalmoscopes. In any embodiment in which the illumination is not provided in the form of an image scanning laser, dilation of the pupil is necessary.

A further variation of the preferred embodiments allows a deviation of either optical module by a few degrees following the optical axis in cases where the patient suffers from strabismus. This option also allows tilting of the apparatus from the optical axis so as to enable examination of the periphery of the retina. This can be accomplished by means of a multi-axis movable table such as those available from New England Affiliated Technologies, Lawrence, Mass.

It will be appreciated by those skilled in the art that the present invention is not limited by a specific optical system with the capacity of retinal angiography. It will further be appreciated that the present invention may be used to perform fluorescein angiography (FA) as well as indocyanine green angiography (ICG) or a combination thereof The present invention is not limited with respect to the dyes that may be used with it. It will be appreciated that the present invention should be adapted for any future agent of contrast found suitable for the eye.

The optical module 101 includes a forward optical assembly 136 which generates an intermediate image of the eye reticulum. According to the present example, forward optical assembly 136 is divided into five lenses by way of convenience, while it will be appreciated that it may be implemented by a varying number of lenses. Forward optical assembly 136 provides a wide angle view of the eye fundus even through an undilated, 2 mm wide, pupil. A 20° field of view is also provided by forward optical assembly 136. It will be appreciated that with appropriate modification of the optical design the field may be widened to a range of 20–120°.

Image relay optics 138 transform the intermediate image generated by forward optical assembly 136 into a format suitable for projecting onto image capturing element 130, such as a conventional CCD detector. Image capturing element 130 is positioned at the focal plane of the imaging lens so as to achieve a sharp image.

According to the invention, each of the lenses can be coated by various coatings such as anti-reflective coating and the like.

It will be appreciated by those skilled in the art that since a spherical lens is considered a particular case of an aspherical lens, it is also possible to provide a lens imaging module according to the invention, which consists of at least one aspherical element. Furthermore, the various dimensions of the above lenses may change when using different transparent materials such as special glass, plastic and the like.

It will be appreciated that the present invention relates to an apparatus capable of performing simultaneous bilateral retinal angiography and various known optical systems for visualization of the fundus may be used.

Figure 3A:
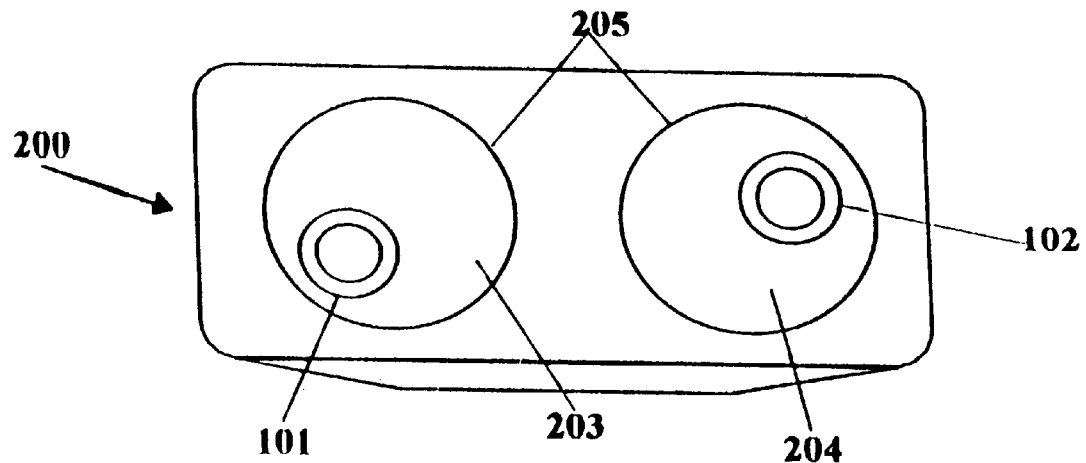
FIGS. 3a–b are, respectively, front and rear views of the optical system block.
Figure 3B:
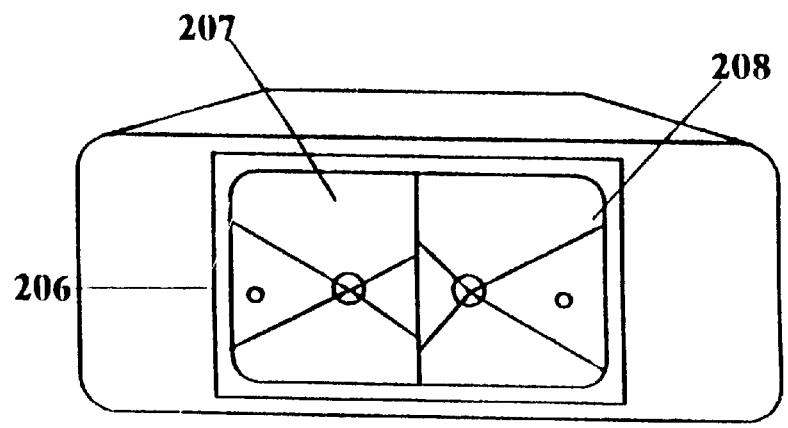

In FIG. 3a, there is shown common optical block 200 in which both optical modules 101, 102 are incorporated. Optical modules 101, 102 have a range of motion in areas 203, 204 as defined by a pair of cylinders 205. FIG. 3b shows a rear view of the apparatus where a single monitor 206 is split to show two images. The image of the fundus of the right eye is shown on side 207, while side 208 refers to the fundus of the left eye.

Figure 4:
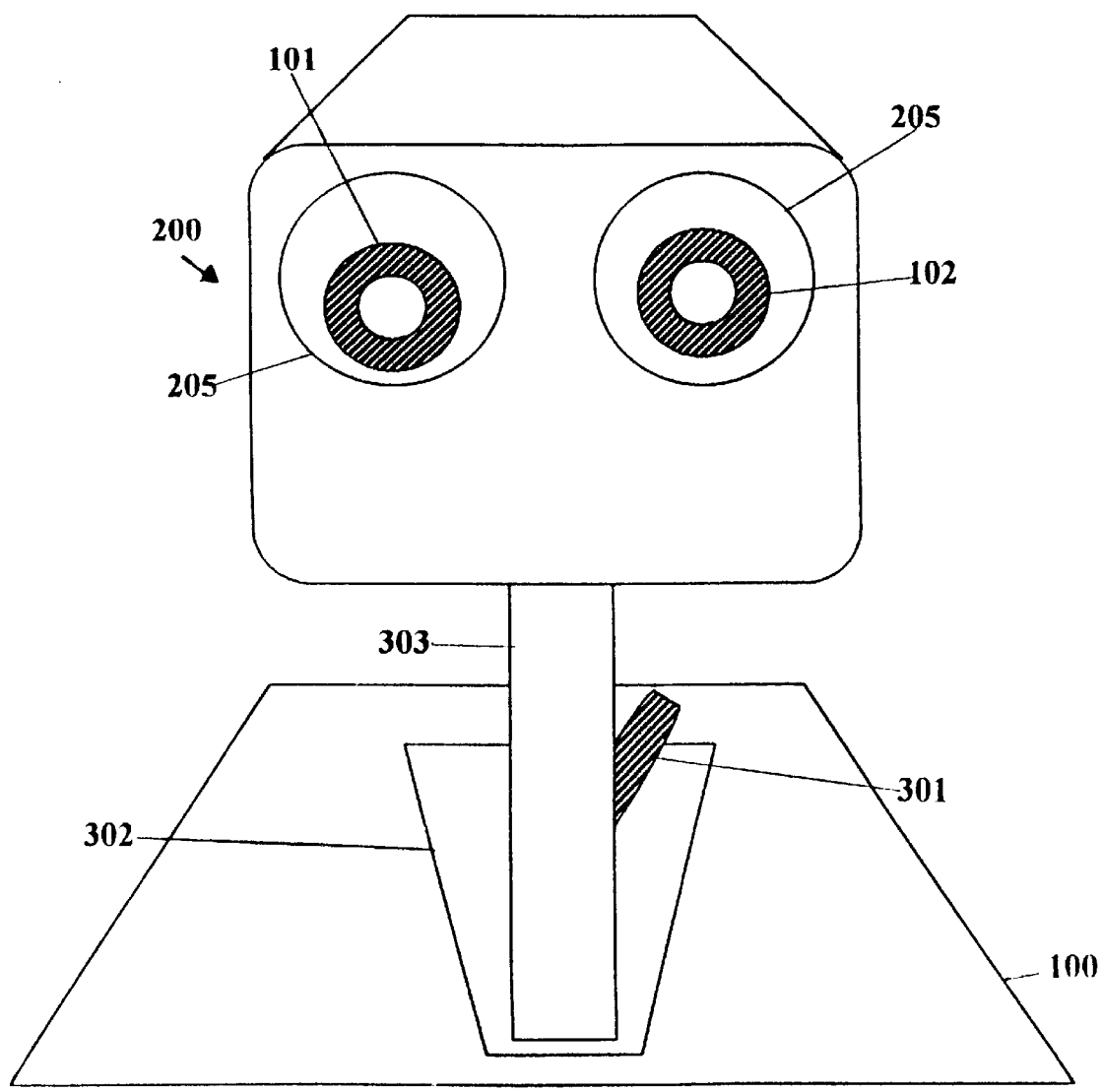
FIG. 4 is a front perspective view of a semi-automated embodiment of the present invention.

Referring now to FIG. 4, there is shown a front perspective of the apparatus in the semi-automated mode of operation. Optical block 200 is attached to the upper extreme of rigid support 303. The lower extreme of rigid support connects the optical block to the mechanical gear box and command console 302. The rough alignment of the apparatus is provided by joystick 301 which moves in X-Y-Z directional planes. Adjustment of right eye module 102 and left eye module 101 in any direction is accomplished by means of electronic commands located in console 302, as seen in FIG. 5.

Figure 5:
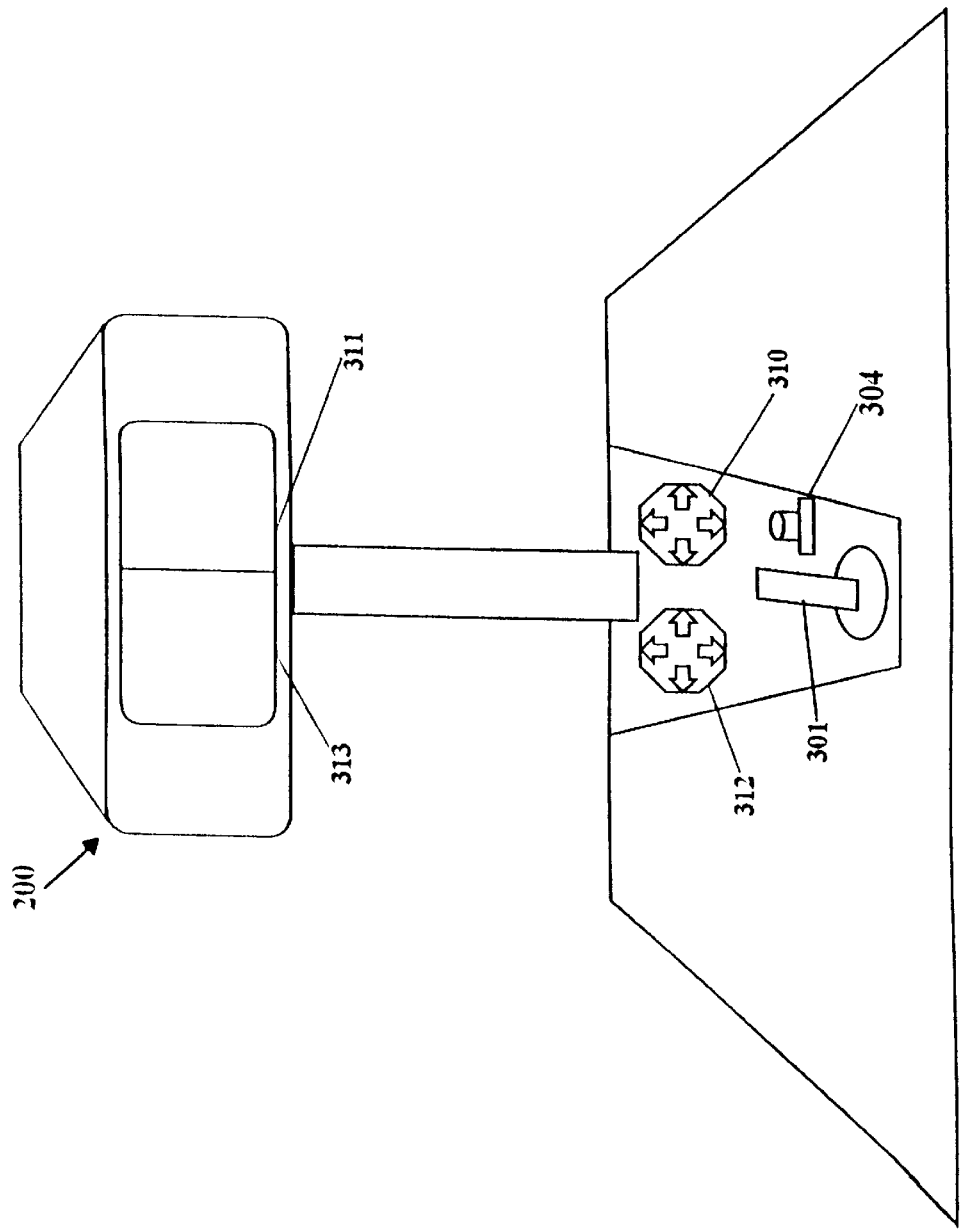
FIG. 5 is a rear perspective view of a semi-automated embodiment of the present invention.

FIG. 5 shows the fine adjustment of modules 101 and 102 which are provided by two motorized systems controlled by electronic commands in control boxes 310 and 312, respectively. In this embodiment the right fundus image is displayed on monitor 313 and the left fundus image is displayed on monitor 311. Trigger 304 located on or near joystick 301, freezes the images allowing acquisition to any image capturing means such as a video camera, CCD sensor, still digital camera or detector with video signal. In addition, a foot pedal is provided (not shown) to allow for optional acquisition of the images by pressing on the pedal.

Figure 6A:
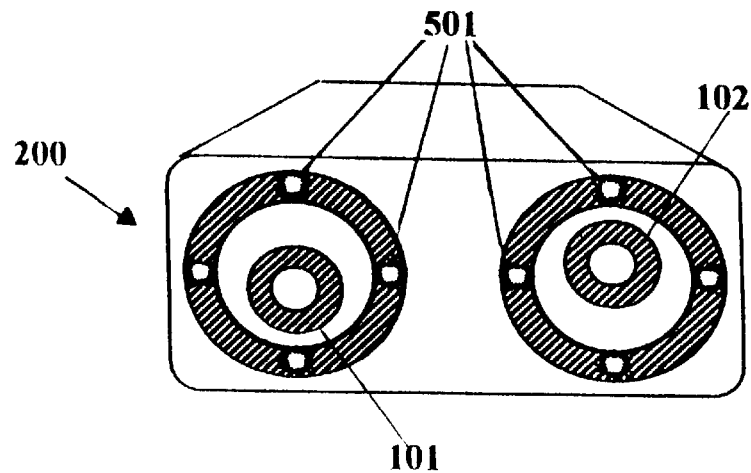
FIGS. 6a–b are, respectively, a front view of the optical system block of a fully-automated embodiment and a rear view of the apparatus as constructed for a fully-automated embodiment.

FIG. 6a shows a front view of the optical system block of the fully-automated embodiment. In this embodiment a plurality of photosensors 501 are located around the front lens of each of modules 101 and 102 which detect the edge of the pupil. The infrared sensors are connected to a microprocessor programmed to identify the difference in the reflected light coming from the iris as compared to the lower level of light coming from the interior of the eye when the beam enters the eye cavity through the pupil. The microprocessor identifies the lower level of reflected light coming from the pupil and activates the electronic commands of the XYZ mechanical system to allow the motor to perform corrections on the alignment of optical modules 101,102 in accordance with the optical axis of the eye.

It will be appreciated that this embodiment of the invention is not limited by the automatic mode of the photosensors and the automation can be disconnected allowing manual adjustment of the apparatus using control boxes 503 and 504.

Figure 6B:
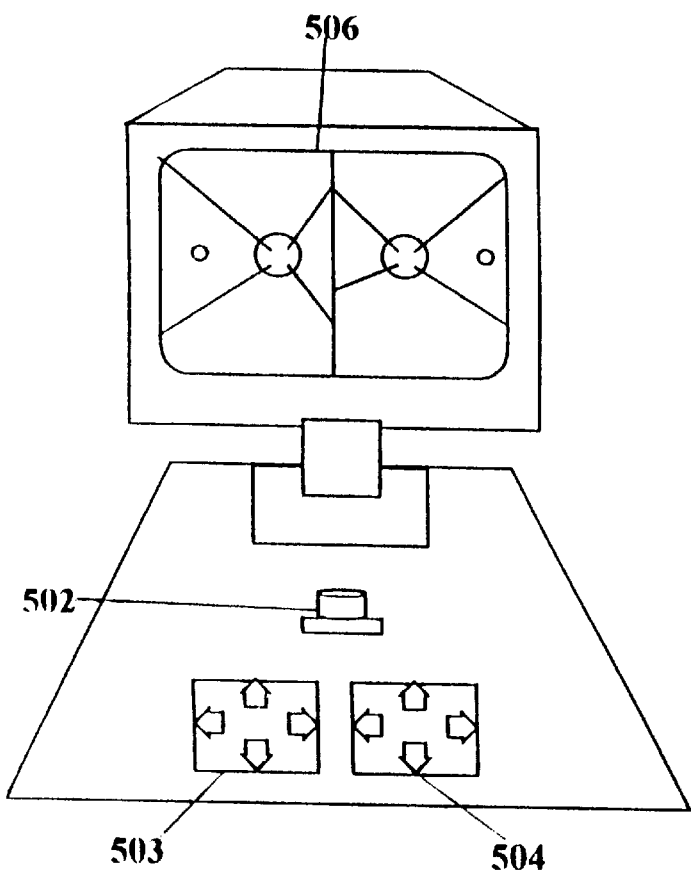

As shown in FIG. 6b, images from modules 101 and 102 are displayed on monitor 506. In a situation in which the operator desires to operate the apparatus in a semi-automatic fashion, control boxes 503 and 504 are used to align the modules on the optical axis. Trigger 502 located on or near control boxes 503 and 504 is depressed to capture the simultaneous pair of images. Capture of images is also possible by means of a foot pedal provided in parallel with the trigger for the convenience of the operator.

Figure 7:
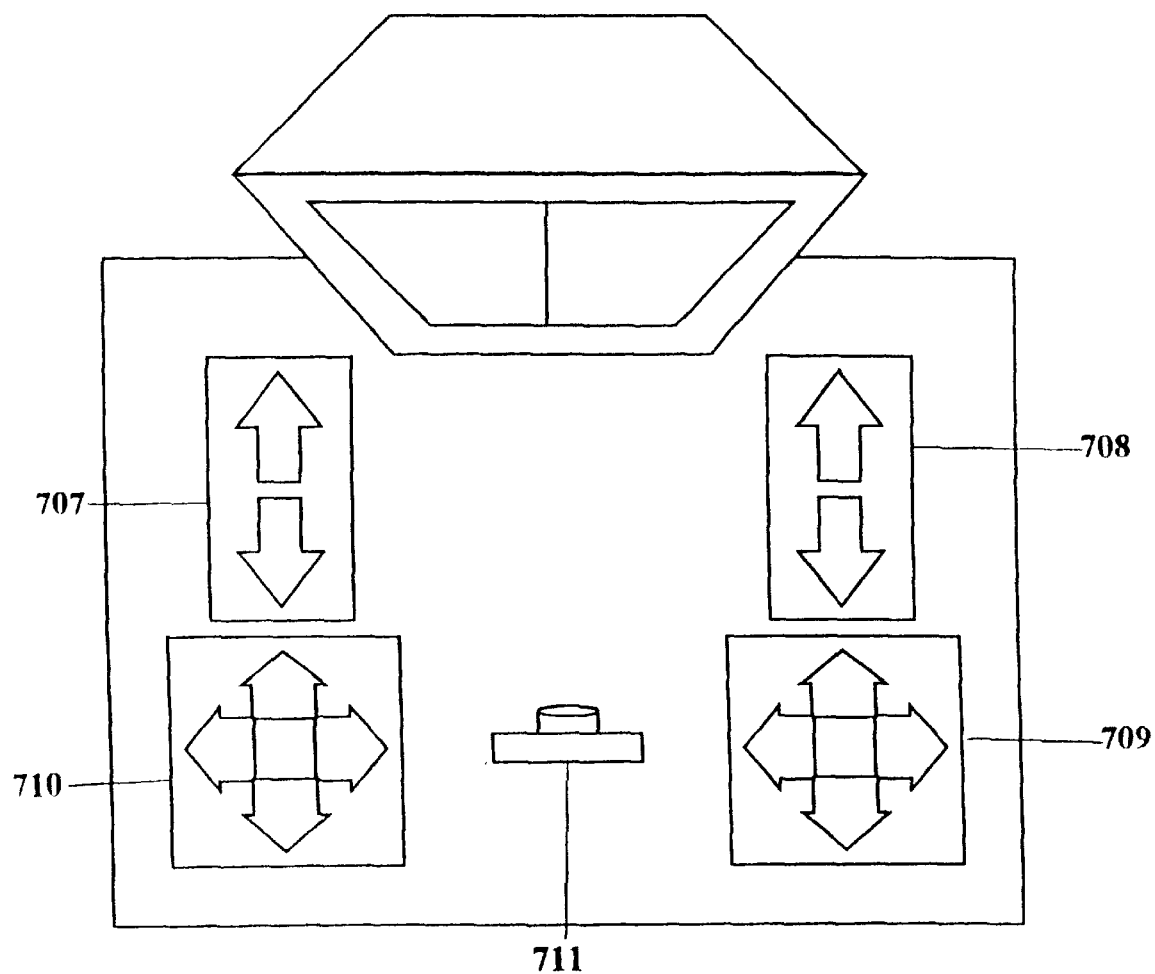
FIG. 7 is a top view of the apparatus of the present invention showing the electrical alignment and focusing command controls.

FIG. 7 shows an overhead view of the semi-automated embodiment wherein the electronic commands for fine adjustment of right module 101 are found on control box 710 and control box 709 adjusts left module 102. Command controls 707 and 708 operate the focusing system by electrically moving the parts of the module responsible for image focusing backwards and forwards. Trigger 711 captures the images.

Figure 8:
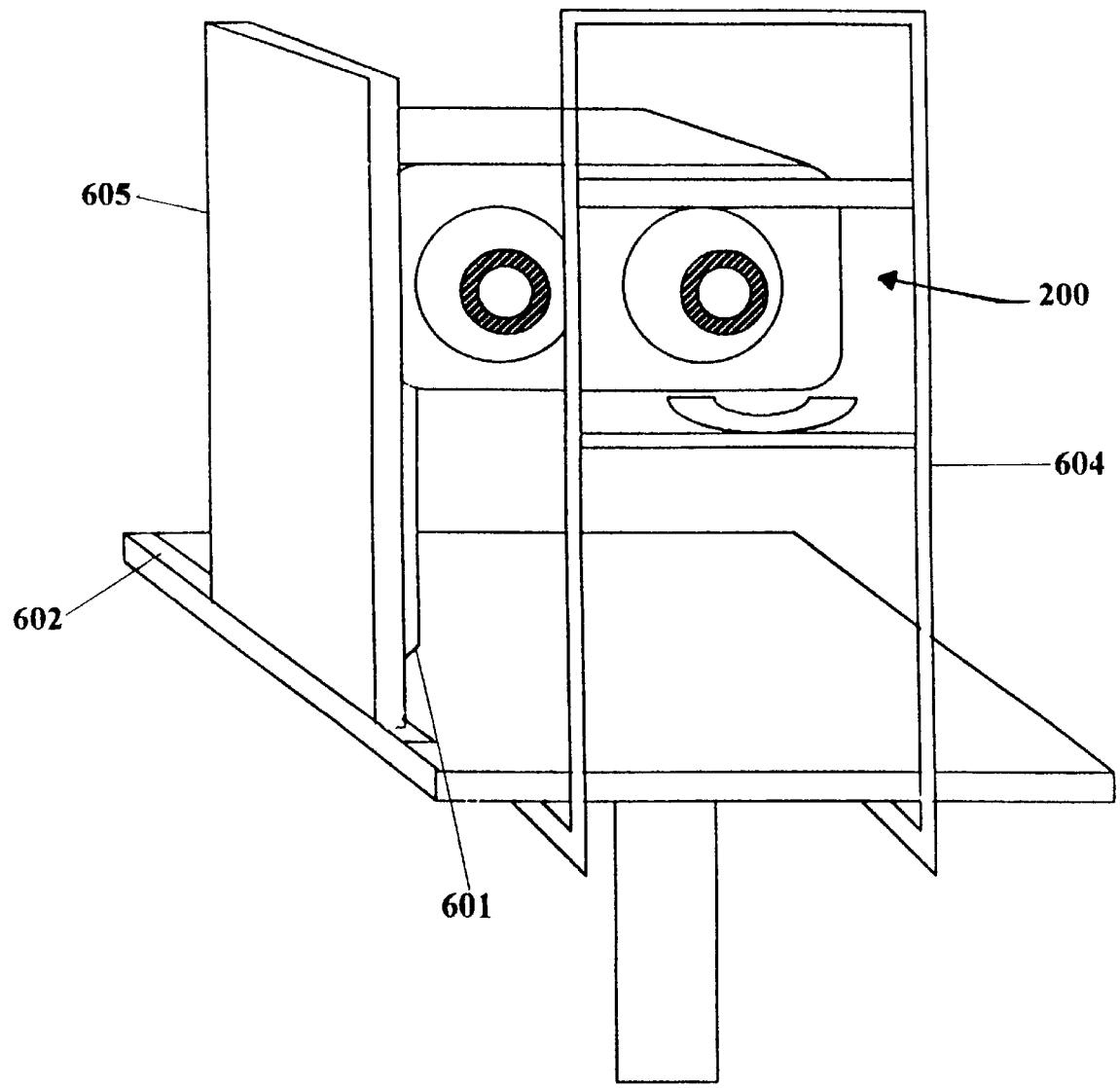
FIG. 8 is a front view of the apparatus mounted on a movable instrument table.

FIG. 8 illustrates a further preferred embodiment wherein optical block 200 is attached to a side track 601 for moving the apparatus in a vertical direction. Horizontal movement is achieved by sliding tower 605 on rail 602. This movement can also be accomplished in an electrical mode of operation (not shown). Chin rest and forehead support 604 is provided for immobilizing the patient's head opposite the apparatus. Chin rest and forehead support 604 can be provided in any of the conventional constructions for such devices.

Figure 9:
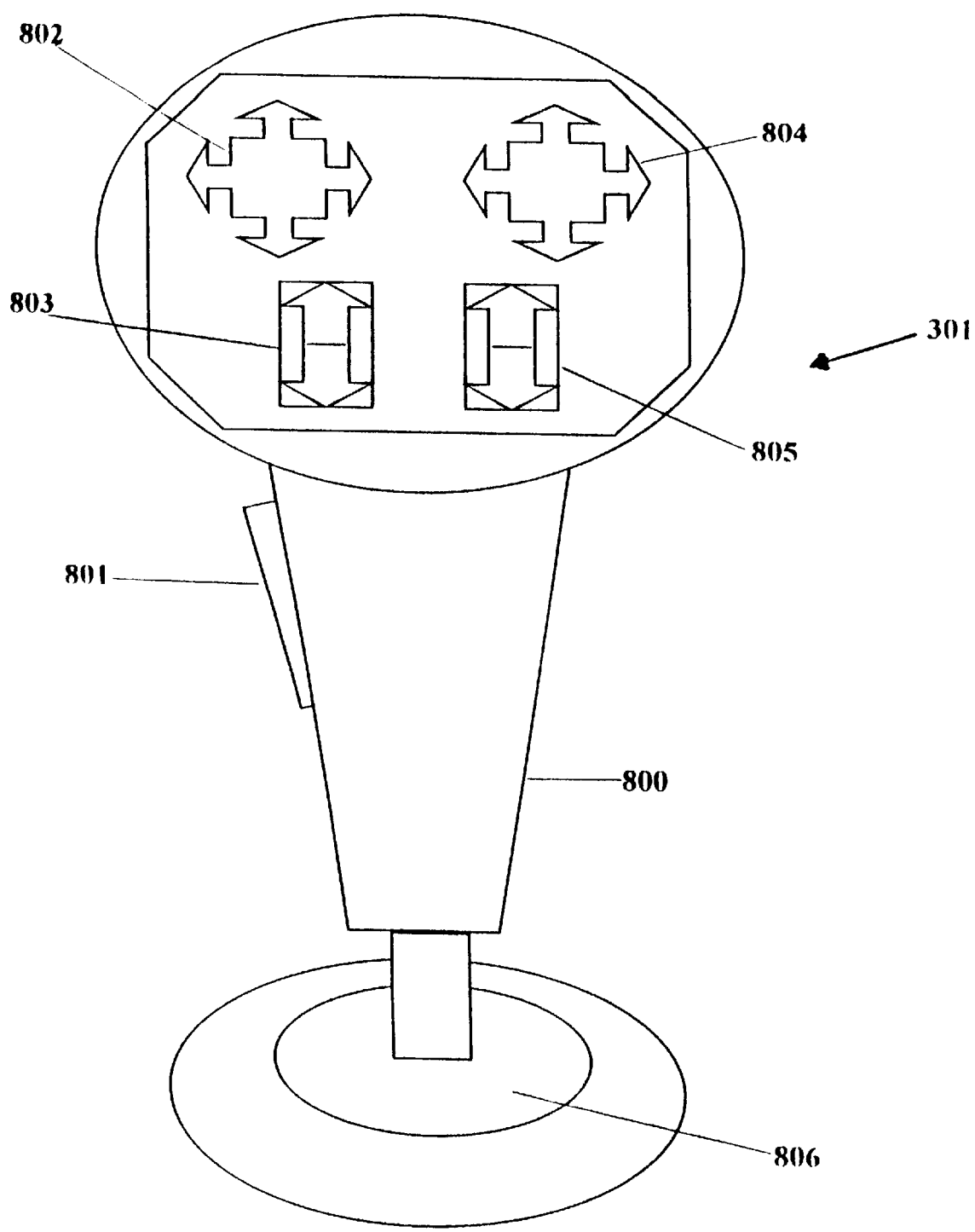
FIG. 9 is a perspective view of a joystick as constructed for the semi-automated embodiment.

FIG. 9 illustrates a preferred embodiment of joystick 301. Joystick 301 controls the depth by displacing the handle 800 within space 806. Controls 802 and 804 move modules 102, 101, respectively, in vertical and horizontal directions. Focusing of the image is accomplished by means of command controls 803 and 805 for the right and left eyes respectively. Trigger 801 is depressed to capture the image.

Figure 10:
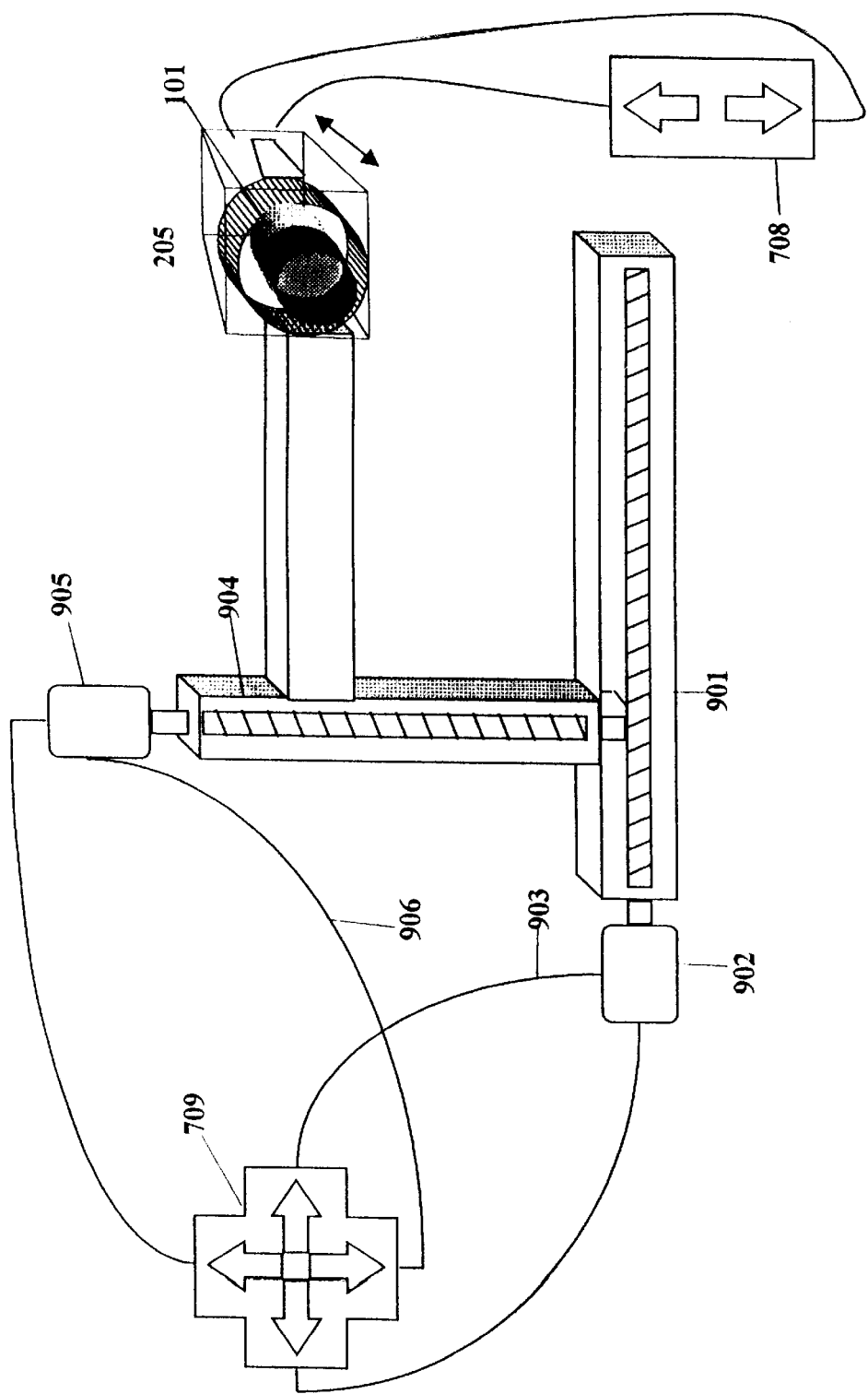
FIG. 10 is a schematic drawing of the electromechanical system for aligning and focusing the apparatus.

FIG. 10 is a schematic drawing of the electromechanical system for moving modules 101 and 102 over the front panel of optical block 200 within the defined space of cylinders 205. A module 101, by way of example, is attached to screw axis 904 which is attached at an extreme to small motor 905 which is supplied with DC current through cable 906. This allows vertical movement. Screw axis 901 is connected to small motor 902 receiving DC current through cable 903. This is responsible for the horizontal displacement of the module. XYZ-directional movement is accomplished by means of a multi-axis table such as those provided by New England Affiliated Technologies, Lawrence, Mass.

Figure 11:
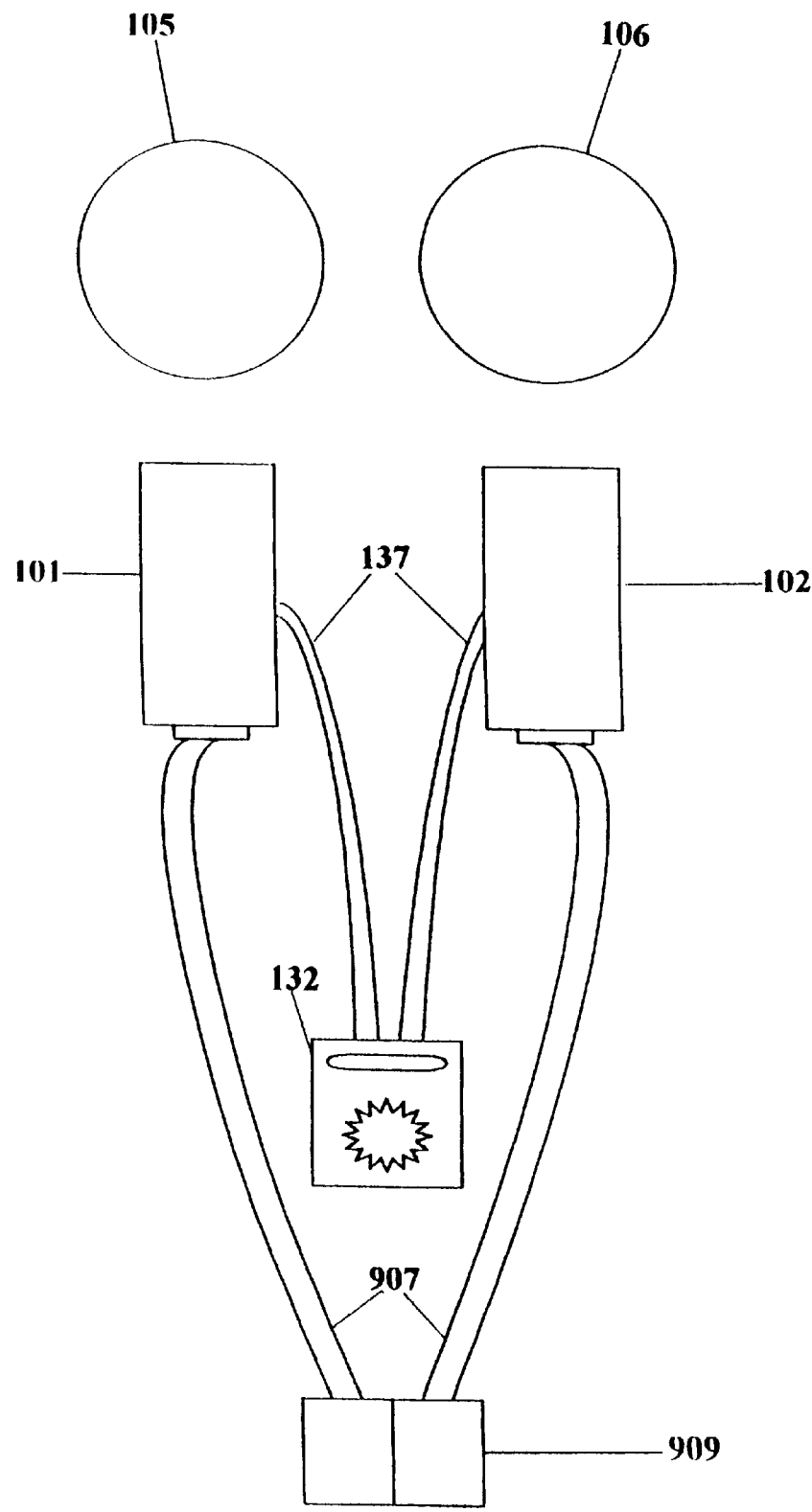
FIG. 11 is a schematic drawing of a fiber optic imaging system for use with the present invention.

FIG. 11 is a schematic drawing of a fiber optic imaging system for use with the present invention. In this embodiment, the optical modules 101 and 102 are each connected at their far end to one of coherent fiber image guides 907 (available from Schott Fiber Optics, Inc. Southbridge, Mass.). Fiber image guides 907 connect at their other extreme to camera 909. Each fiber image guide carries the image from its corresponding optical module to a common camera 909 which divides the single frame in half, each half corresponding to an image from one of optical modules 101,102.

An image conducting rod may be added to the optical system between the lenses and fiber image guides 907. The image conducting rod is a solid fiber optic element which can be used to transmit images over short distances and which can be manufactured with conical image guides for reducing or increasing the effective optical cross-sections and aperture angles.(also available from Schott Fiber Optics, Inc. Southbridge, Mass.) In this way, the image conducting rod may replace some of the optical lenses in the optical module, even to the point of leaving only primary ophthalmic lens 139 (see FIG. 2) which generates a first image of the eye.

Thus, the present invention provides an apparatus for simultaneous bilateral retinal digital angiography which is convenient to for the operator to use, gives rapid results, is economical and minimizes patient discomfort.

Having described the invention with regard to certain particular embodiments thereof, it is to be understood that the description is not meant as a limitation, since further modifications will now become apparent to those skilled in the art and it is intended to cover such modifications as fall within the scope of the appended claims.

What is claimed is:

1. An apparatus for diagnosis of retinal disorders comprising:
   a pair of means for optically forming independent retinal images, each image forming means being separately adjustable for observation of an eye, each of said image forming means comprising:
   means for alignment of said image forming means in front of the eye;
   means for illumination of the interior of the eye; and
   means for focusing said retinal image, at least one display means for displaying each of said pair of retinal images enabling simultaneous bilateral retinal digital angiography for diagnostic analysis, wherein said alignment means is operable in at least one of a plurality of modes selected from manual, semi-automatic and automatic modes.

2. The apparatus of claim 1 wherein said alignment and focusing means operate in a manual mechanical fashion.

3. The apparatus of claim 2 wherein said pair of manual mechanical alignment means are controlled by at least one joystick mechanism.

4. The apparatus of claim 2 further comprising motorized means for adjusting said alignment and focusing means providing a semi-automated apparatus.

5. The apparatus of claim 4 wherein said motorized means are controlled by electronic controls.

6. The apparatus of claim 1 wherein said image forming means are narrowed so as to allow accommodation of varied papillary distances.

7. The apparatus of claim 1 wherein said alignment and focusing means comprise:
   a plurality of infrared detectors for alignment of said apparatus with the optical axis of the eye by detecting an edge of the pupil;
   at least one infrared beam for focusing said image by measuring the distance between the retina and the focal plane and providing focusing parameters; and
   motor means responsive to said focusing parameters to maintain focus,
   providing a fully-automated apparatus.

8. The apparatus of claim 7 in which said infrared detectors are arranged in four cardinal points around a front panel of said apparatus.

9. The apparatus of claim 1 wherein said illumination means comprises at least one scanning laser beam for illumination and imaging of the retina.

10. The apparatus of claim 9 wherein at least two scanning laser beams of different wavelengths are provided enabling visualization of at least two different agents of contrast.

11. The apparatus of claim 1 wherein said illumination system comprises at least one viewing light source and strobe lamp in a single housing with two flexible fiber optic bundles emanating therefrom.

12. The apparatus of claim 1 wherein said image forming means comprises a fiber optic imaging bundle connected at its one extreme to a primary ophthalmic lens and at its other extreme to an image capturing means.

13. The apparatus of claim 1 wherein said pair of means for image forming are provided within a common housing such that each means for image forming is independently capable of a free range of motion.

14. The apparatus of claim 1 wherein said display means is provided as a single screen split so as to display a pair of said retinal images.

15. The apparatus of claim 1 further comprising a varied range of barrier and exciter filters for adjusting responsiveness to various agents of contrast.

16. The apparatus of claim 1 wherein said image forming means further comprises a primary ophthalmic lens providing a field of view of between 20°–120°.

17. The apparatus of claim 1 wherein said image forming means can be tilted off of the optical axis to obtain images of the periphery of the fundus.

18. A method for diagnosing retinal disorders comprising the steps of:
   optically forming a pair of independent retinal images using a pair of means for optically forming independent retinal images, each forming means being separately adjustable for observation of an eye, further comprising the steps of:
      aligning said forming means in front of the eye;
      illuminating the interior of the eye;
      focusing said retinal image, and,
   displaying said retinal image enabling simultaneous bilateral retinal digital angiography for diagnostic analysis,
   wherein said aligning step is performed in at least one of a plurality of modes selected from manual, semi-automatic and automatic modes.

19. The method of claim 18 wherein said steps of aligning and focusing said retinal image are accomplished in a manual mechanical fashion.

20. The method of claim 18 wherein said steps of alignment and focusing are accomplished in a motorized semi-automated fashion.

* * * * *